United States Patent [19]

Cabri et al.

[11] Patent Number: 5,621,096
[45] Date of Patent: Apr. 15, 1997

[54] PROCESS FOR PREPARING PENEMS

[75] Inventors: Walter Cabri, Rozzano; Angelo Bedeschi, Milan, both of Italy

[73] Assignee: Pharmacia S.p.A., Milan, Italy

[21] Appl. No.: 558,209

[22] Filed: Nov. 16, 1995

Related U.S. Application Data

[63] Continuation of Ser. No. 381,570, Jan. 31, 1995, abandoned.

[30] Foreign Application Priority Data

Feb. 9, 1904 [GB] United Kingdom .................. 9402459

[51] Int. Cl.$^6$ .................... C07D 499/00; C12P 37/00
[52] U.S. Cl. ...................... 540/310; 435/43; 435/197; 435/198
[58] Field of Search ............... 435/43; 540/310

[56] References Cited

U.S. PATENT DOCUMENTS 5,364,768  11/1994  Altamura et al. ..................... 435/43

OTHER PUBLICATIONS

Klibanov "Enzymatic Reactions in Organic Media", *Protein Engineering Applications and Science, Medicine, and Industry* (1986).
The Journal of Antibiotics, vol. 36, No. 7, pp. 938–941, Jul. 1983, G. Franceschi, et al., "Synthesis And Biological Properties of Sodium (5R,6S,8R)–6α–Hydroxyethyl–2–Carbamoyloxymethyl–2–Penem–3–Carboxylate (FCE 22101) and Its Orally Absorbed Esters FCE 22891".
Chem. Pharm. Bull., vol. 40, No. 8, pp. 2227–2229, Aug. 1992, Hazuki Nagai, et al., "Facile Enzymatic Preparation of Enantiomeric β–Lactams".

Tetrahedron Letters, vol. 34, No. 21, pp. 3491–3492, Mar. 1993, Walter Cabri, et al., "The Total Sysnethesis of Ritipenems. Construction of Penem Thiazoline Ring By Incorporation of Two 2C Units of Glycolic Acid."

*Primary Examiner*—Mukund J. Shah
*Assistant Examiner*—Pavanaram K. Sripada
*Attorney, Agent, or Firm*—Oblon, Spivak, McClelland, Maier & Neustadt, P.C.

[57] ABSTRACT

The invention provides a process for the preparation of the compound of formula I

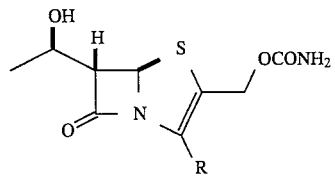

wherein R is carboxy group or a carboxylate anion, by enzymatic hydrolysis with a lipase or an acylase in an alcoholic solution, of a compound of the formula II

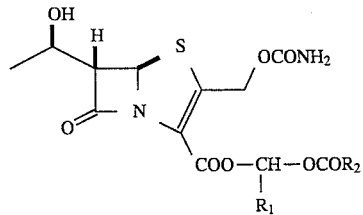

wherein $R_1$, represents a hydrogen atom or a $C_1$–$C_6$ alkyl group, and $R_2$ is a hydrogen atom, an alkyl, alkenyl, phenyl, phenylalkyl or phenylalkenyl group having from 1 to 18 carbon atoms or an alkoxy group.

5 Claims, No Drawings

PROCESS FOR PREPARING PENEMS

This application is a continuation of application Ser. No. 08/381,570, filed on Jan. 31, 1995, now abandoned.

The invention relates to a process for the preparation of penems starting from penem esters by means of enzymatic cleavage.

Penems of formula (I) and (II) are known as antibacterials agents as described in *J. Antibiotics* 1983, 36, 938.

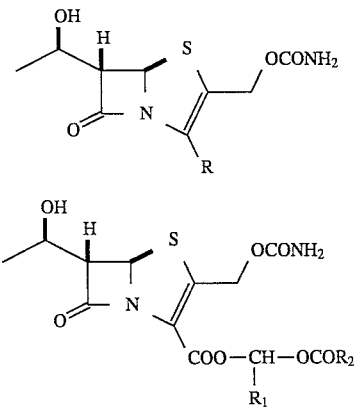

wherein R, $R_1$ and $R_2$ are as defined herein below.

U.K. pat. appl. No. 2206578-A describes a method for preparing compounds of formula (I) from compounds of formula (II) by means of enzymatic hydrolysis carried out in aqueous buffered solutions.

It is also known in the previous art that certain hydrolytic enzymes, such as lipases, are able to perform reactions also in diisopropylether on azetidinones (see for instance *Chem. Pharm. Bull.* 1992, 40, 2227).

The Present invention provides a process for the preparation of a compound of formula I

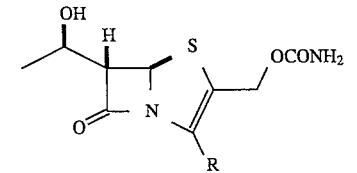

wherein R is carboxy group or a carboxylate anion, by enzymatic hydrolysis with a lipase or an acylase in an alcoholic solution, of a compound of the formula II

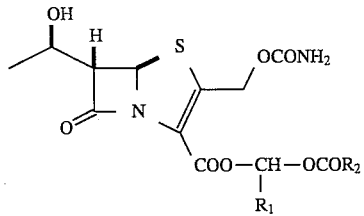

wherein $R_1$ represents a hydrogen atom or a $C_1$–$C_6$ alkyl group, and $R_2$ is a hydrogen atom, an alkyl, alkenyl, phenyl, phenylalkyl or phenylalkenyl group having from 1 to 18 carbon atoms or an alkoxy group.

The present invention provides a simpler an easier work-up for the preparation of compounds of formula I than that of the prior art, after the selective and cheap enzymatic hydrolysis of compounds of formula II as defined above.

In other words, the process of the invention allows the final product to be obtained under very mild conditions, in very high yields, without undesired by-products, and, by simple solvent removal and direct crude crystallisation, in high purity.

For $R_1$ and $R_2$ of the compounds of formula II, alkyl is preferably methyl, ethyl, propyl, butyl; alkenyl is preferably allyl, methallyl; phenylalkenyl is preferably styryl; phenylalkyl is preferably phenylethyl, phenylpropyl, and alkoxy is methoxy or ethoxy.

More preferred values of $R_1$ are a hydrogen atom or a methyl group, and $R_2$ represents a methyl, ethyl or methoxy group.

Most preferably, $R_1$ is a hydrogen atom and $R_2$ represents a methyl group.

The starting materials of formula II may be prepared according known procedures, e.g as described in Tetrahedrons Letters 1993, 34, 3491.

Hydrolytic enzymes suitable for use in the present invention are for example Lipase A6 from *Aspergillus niger* (Amano), Lipase B from *Penicillum Liliacinum* (FICE), Lipase from Wheat Germ (Sigma), Lipase OF from *Candida Cilindracea* (Sankyo), Lipase from *Rhizopus Delamar* (Sigma), or Acilase I from Porcine kidney (Serva) as such or immobilized or supported according to known techniques to resins, glass, cellulose, or diatomaceous earths.

Preferred hydrolytic enzymes are Lipase A6 from *Aspergillus niger* (Amano), Lipase B from *Penicillum Liliacinum* (FICE), Lipase OF from *Candida Cilindracea* (Sankyo) and Acilase I from Porcine kidney (Serva), the most preferred being Lipase A6 from *Aspergillus niger* (Amano), and Lipase B from *Penicillum Liliacinum* (FICE), and Lipase OF from *Candida Cilindracea* (Sankyo).

Preferred supporting media include resins and diatomaceous earths, the most preferred diluents being the diatomaceous earths.

The above said enzymes are able to hydrolyse the esters of formula II in an alcoholic solution containing up to 10% of water, preferably the alcohol being selected from secondary or tertiary $C_3$–$C_6$ alcohols, more preferably being i-propyl alcohol, t-butyl alcohol, s-butyl alcohol, t-amyl alcohol. The most preferred solvent is t-amyl alcohol. The reaction may be carried out dissolving/suspending the compound of formula II in the above defined water containing alcoholic solution, in the presence of the enzyme as such, or preferably supported on a suitable supporting medium, as defined above, at a temperature from about 10° C. to 60° C., preferably from about 20° C. to 50° C., for about 0.5 to 48 hours, operating in batch or column, according to the quantity of the enzyme present in the reaction mixture, and to the ratio between the quantity of the enzyme as such or in the supported form, and the quantity of substrate present in the reaction mixture.

At the end of the reaction, the reaction product may be easily recovered, simply by removing the solvent, after filtration of the insoluble supported enzyme.

EXAMPLE 1

(1'R) 6-[1'-hydroxyethyl]-2-carbamoyloxymethyl-penem-3-carboxylic acid

Celite 535 (Fluka, 6 g) were added to a solution of Lipase A6 from *Aspergillus niger* (1 g) in 0.1N phosphate buffer pH 7.0 (10 mL). The mixture was spread on a watch glass and left drying at room temperature with occasional mixing until dry.

The above supported enzyme (7 g) was added at room temperature to a solution of acetoxymethyl (1'R) 6-[1'-hydroxyethyl]-2-carbamoyloxymethyl-penem-3-carboxylate (2.5 g) in tert-amyl alcohol (75 mL), containing 10% v/v of water. After 24 hours the mixture was filtered, and the solid was washed with tert amyl alcohol. The organic filtrates were evaporated in vacuo so obtaining the crude product. The crude product was crystallized upon addition of water (18 mL) at 0°–5° C. to yield 1.8 g of the pure title product.

EXAMPLE 2

(1'R) 6-[1'-hydroxyethyl]-2-carbamoyloxymethyl-penem-3-carboxylic acid 30 g of Amberlite XAD-7 were added to a solution of Lipase A6 from *Aspergillus niger* (1 g) in 0.01N phosphate buffer (125 mL, pH=7.0). The resin mixture was gently stirred overnight at room temperature. Then the resin was filtered and washed with the same buffer (125 mL), and air dried.

The immobilized enzyme resin was added to a solution of acetoxymethyl (1'R) 6-[1'-hydroxyethyl]-2-carbamoyloxymethyl-penem-3-carboxylate (2.5 g) in tert-amyl alcohol (75 mL), containing 10% v/v of water. After 24 hours the mixture was filtered, and the solid was washed with tert amyl alcohol. The organic flitrates were evaporated in vacuo so obtaining the crude product. After water crystallization 0.6 g of the title product were obtained.

EXAMPLE 3

(1'R) 6-[1'-hydroxyethyl]-2-carbamoyloxymethyl-penem-3-carboxylic acid

The reaction was performed as in example 1, except that unsupported Lipase A6 was used. There were obtained 1.4 g of the title product.

EXAMPLE 4

(1'R) 6-[1'-hydroxyethyl]-2-carbamoyloxymethyl-penem-3-carboxylic acid

The reaction was performed as in example 1, except that Lipase B (FICE) from *Penicillum Liliacinum* was used. There were obtained 1.1 g of the title product.

EXAMPLE 5

(1'R) 6-[1'-hydroxyethyl]-2-carbamoyloxymethyl-penem-3-carboxylic acid

The reaction was performed as in example 1, except that tert-butyl alcohol, containing 10% v/v water was used as solvent. There were obtained 0.5 g of the title product.

EXAMPLE 6

(1'R) 6-[1'-hydroxyethyl]-2-carbamoyloxymethyl-penem-3-carboxylic acid

The reaction was performed as in example 1, except that Lipase OF from *Candida cilindracea* (Sankyo) was used. There were obtained 0.9 g of the title product.

EXAMPLE 7

(1'R) 6-[1'-hydroxyethyl]-2-carbamoyloxymethyl-penem-3-carboxylic acid

The reaction was preformed as in example 1, except that acetone, containing 10% v/v water was used as solvent. After 96 hours reaction, there were obtained 1.1 g of the title product.

EXAMPLE 8

(1'R) 6-[1'-hydroxyethyl]-2-carbamoyloxymethyl-penem-3-carboxylic acid

The reaction was performed as in example 1, except that acetonitrile, containing 10% v/v water was used as solvent. After 96 hours reaction, there were obtained 0.8 g of the title product.

We claim:

1. A process for the preparation of a compound of the formula I

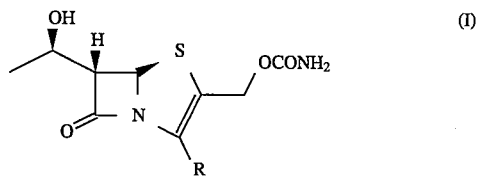

wherein R is a carboxy group or a carboxylate anion, by enzymatic hydrolysis with a lipase or an acylase immobilized or supported in an alcoholic solution, containing up to 10% of water, of a compound of the formula II

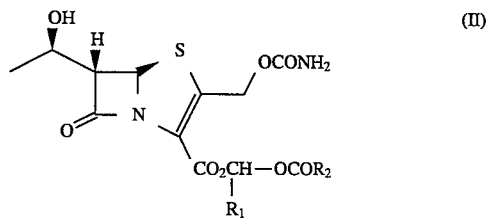

wherein $R_1$ represents a hydrogen atom or a $C_1$–$C_6$ alkyl group, and $R_2$ is a hydrogen atom, an alkyl, alkenyl, phenyl, phenylalkyl or phenylalkenyl group having from 1 to 18 carbon atoms or an alkoxy group.

2. A process according to claim 1, in which $R_1$ is hydrogen or methyl group and $R_2$ is methyl, ethyl or methoxy group.

3. A process according to claim 1 or 2, in which the enzymatic hydrolysis is carried out with Lipase A6 from *Aspergillus niger*, Lipase B from *Penicillum Lilacinum*, or Lipase OF from *Candida Cilindracea*.

4. A process according to any one of the preceding claims, in which the enzymatic hydrolysis is carried out with the lipase supported to resins or diatomaceous earths.

5. A process according to any of the preceding claims, in which the enzymatic hydrolysis is carried out in i-propyl alcohol, i-butyl alcohol, s-butyl alcohol, or t-amyl alcohol.

* * * * *

UNITED STATES PATENT AND TRADEMARK OFFICE
CERTIFICATE OF CORRECTION

PATENT NO. : 5,621,096
DATED : April 15, 1997
INVENTOR(S) : Walter CABRI, et al.

It is certified that error appears in the above-indentified patent and that said Letters Patent is hereby corrected as shown below:

On the title page, item [30], Foreign Application Priority Data should be:

[30]

--Feb. 9, 1994  [GB]  United Kingdom .......... 9402459--

Signed and Sealed this

Twelfth Day of August, 1997

Attest:

BRUCE LEHMAN

Attesting Officer

Commissioner of Patents and Trademarks